(12) United States Patent
Dunn et al.

(10) Patent No.: US 7,877,003 B2
(45) Date of Patent: Jan. 25, 2011

(54) DEVICES, SYSTEMS, AND METHODS REGARDING IMAGES

(75) Inventors: Sheila Bergeron Dunn, Mason, NH (US); Michael C. Messina, Hooksett, NH (US)

(73) Assignee: Microscan Systems, Inc., Renton, WA (US)

( * ) Notice: Subject to any disclaimer, the term of this patent is extended or adjusted under 35 U.S.C. 154(b) by 186 days.

(21) Appl. No.: 12/141,150

(22) Filed: Jun. 18, 2008

(65) Prior Publication Data

US 2009/0003810 A1    Jan. 1, 2009

Related U.S. Application Data

(60) Provisional application No. 60/945,179, filed on Jun. 20, 2007.

(51) Int. Cl.
*G03B 15/03* (2006.01)
*H04N 7/18* (2006.01)

(52) U.S. Cl. .............................. 396/4; 348/131; 362/13

(58) Field of Classification Search ................ 396/4, 396/155, 166, 173, 175, 182; 362/11–13; 348/131
See application file for complete search history.

(56) References Cited

U.S. PATENT DOCUMENTS

| | | | |
|---|---|---|---|
| 3,614,449 A | 10/1971 | Ward, III | |
| 4,594,645 A | 6/1986 | Terashita | |
| 4,653,875 A | 3/1987 | Hines | |
| 5,172,005 A | 12/1992 | Cochran et al. | |
| 5,461,417 A | 10/1995 | White | |
| 5,539,485 A | 7/1996 | White | |
| 5,604,550 A | 2/1997 | White | |
| 5,684,530 A | 11/1997 | White | |
| 5,761,540 A | 6/1998 | White | |
| 5,903,394 A | 5/1999 | Sipotz, Jr. | |
| 6,324,024 B1 | 11/2001 | Shirai et al. | |
| 6,552,783 B1 * | 4/2003 | Schmidt et al. | .......... 356/237.4 |
| 2006/0175409 A1 | 8/2006 | Reichenbach | |
| 2008/0106794 A1 | 5/2008 | Messina | |
| 2008/0137323 A1 | 6/2008 | Pastore | |
| 2008/0137325 A1 | 6/2008 | Pastore | |

(Continued)

FOREIGN PATENT DOCUMENTS

EP    0685140    12/1995

(Continued)

OTHER PUBLICATIONS

AIM, "Direct Part Mark (DPM) Quality Guideline", Dec. 12, 2006, 20 page(s), AIM, Inc.

(Continued)

*Primary Examiner*—W. B. Perkey
*Assistant Examiner*—Autumn Parker
(74) *Attorney, Agent, or Firm*—Blakely Sokoloff Taylor & Zafman LLP

(57) ABSTRACT

An illumination and/or imaging system including a dome, a crown, and multiple light sources for illuminating an object. The multiple light sources can include dome lights, diffuse on-axis sources, diffuse off-axis sources, medium-angle direct light sources and low-angle direct light source. The medium- and low-angle sources can illuminate the object from one direction or from multiple directions simultaneously.

19 Claims, 16 Drawing Sheets

U.S. PATENT DOCUMENTS

2008/0170380 A1   7/2008   Pastore

FOREIGN PATENT DOCUMENTS

| EP | 1 455 179 A1 | 9/2004 |
|---|---|---|
| WO | WO 99/22224 | 5/1999 |
| WO | WO 02/075637 A1 | 9/2002 |
| WO | WO 2005/043449 A1 | 5/2005 |
| WO | WO2008039541 | 4/2008 |

OTHER PUBLICATIONS

PCT/US2008/007673, International Search Report and Written Opinion of the International Searching Authority, mail date Oct. 13, 2008.

PCT/US2007/021064, International Search Report and Written Opinion of the International Searching Authority, mail date May 15, 2008, 10 pages.

* cited by examiner

SECTION B-B
8000

DETAIL D

DEVICES, SYSTEMS, AND METHODS REGARDING IMAGES

CROSS-REFERENCES TO RELATED APPLICATIONS

This application claims priority to, and incorporates by reference herein in its entirety, U.S. Provisional Patent Application Ser. No. 60/945,179, filed 20 Jun. 2007.

BACKGROUND

Robotic assembly machines often utilize video cameras to observe a component, part or work piece being handled, machined or assembled. For instance, in the assembly of electronic components, chips or wafers are often assembled into printed circuit boards by robots utilizing video cameras to position the components and/or to inspect the assembled device for defects throughout the process. In the microelectronics industry, solder pads on surface-mount devices are often observed by machine vision systems for assembly and manufacturing purposes. The accuracy and reliability of a machine vision system is critical for proper alignment of the numerous components which are to be mounted on a printed circuit board. For optimum alignment, solder pads must be clearly observed in high contrast with their background.

Proper illumination of many different shiny and uneven surfaces, such as solder connections, foil packaging, ball bearings, etc., is critical if high quality robotics assembly is to be achieved. However, such shiny and uneven surfaces are difficult to illuminate for accurate video imaging, and this creates a need for improved illumination of such objects being observed by machine vision cameras.

When using previously available illumination systems to illuminate work pieces having uneven, highly reflective surfaces, the uneven reflection of light from these surfaces frequently produces erroneous images and signals when viewed through the camera, thereby possibly resulting in an erroneous signal or incorrect/inaccurate measurement. Errors of one or two thousandths of an inch in a fiducial location measurement for a single component are sufficient to ruin a large and expensive circuit board. Furthermore, previously available illumination systems for robotics handling of items have not produced a light which is uniform over the entire object being observed. As a result, the reflected image suffers from erroneous shadows, glints and glare thereby rendering it difficult to determine the precise location or quality of the object.

To date, many illumination devices have been developed to provide substantially uniform illumination of an object to be viewed. For example, U.S. Patent Publication No. 2008/0106794 to Messina, which is incorporated herein by reference in its entirety, discloses illuminating a component via a beamsplitter comprising at least three distinct light-reflection zones. The beamsplitter can illuminate a component with light energy reflected from each of a plurality of distinct light reflection zones.

Similarly, U.S. Pat. No. 5,761,540 to White, which is also incorporated herein in its entirety, discloses an illumination device for illuminating an object to be observed by a machine vision camera or the like with a continuous diffuse wide-angle light along the observation axis of the machine vision camera. A diffuser is mounted parallel to the observation axis, but is separated from a beamsplitter by a microlouver filter so that the microlouver filter prevents diffused light from the diffuser from directly illuminating any point of interest on the surface of the object to be observed.

SUMMARY

An illumination and/or imaging system including a dome, a crown, and multiple light sources for illuminating an object. The multiple light sources can include dome lights, diffuse on-axis sources, diffuse off-axis sources, medium-angle direct light sources and low-angle direct light source. The medium- and low-angle sources can illuminate the object from one direction or from multiple directions simultaneously.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DETAILED DESCRIPTION

Figure 1:
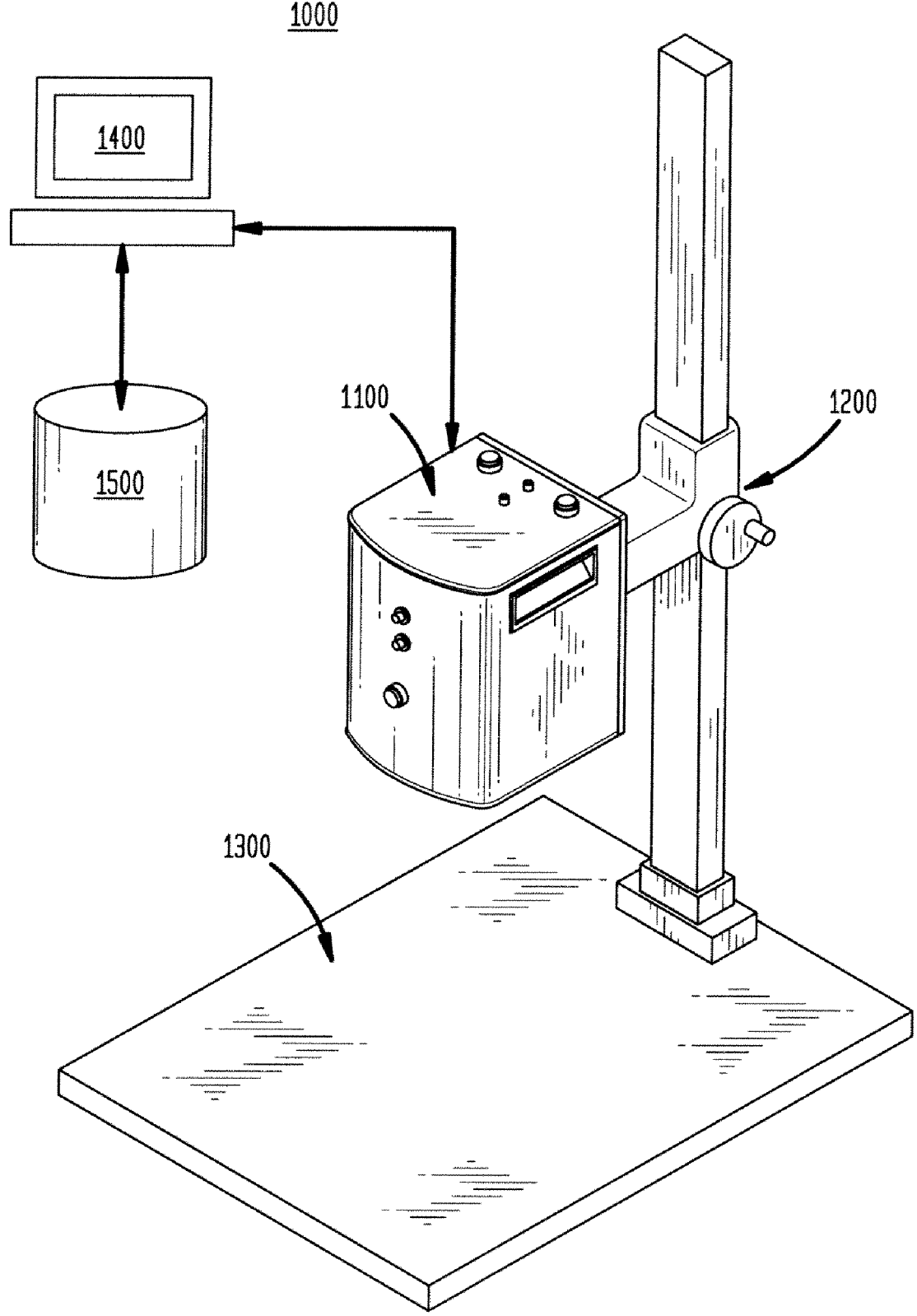
FIG. 1 is a perspective view of an exemplary embodiment of a system 1000.

Certain exemplary embodiments can provide a system, which can comprise a dome. The dome can have a truncated four-sided pyramid shape. The system can comprise a crown adapted to be operatively coupled to an apex portion of the dome. The system can comprise a plurality of light sources adapted to illuminate an object.

Camera based inspections can use lighting that is customized for a given application. Customized lighting for an application can be challenging when parts vary in geometry and/or finish. Certain exemplary embodiments can provide a self-contained imaging module with a plurality of different lighting techniques for machine vision applications to customize lighting applications (e.g., machine vision applications).

A self-contained imaging system can comprise a camera adapted to obtain images of an illuminated object. The object can be illuminated by a set of controlled light sources, which can comprise:

a diffuse on-axis light source that can be directed toward a beamsplitter, which can reflect a portion of light from the diffuse light source such that light rays that are approximately parallel to an axis of view of the camera;

a light source that can be directed toward a dome of the system, which can reflect diffuse off-axis light rays to define an angle that is between approximately 45 degrees and 90 degrees relative to a plane that is substantially perpendicular to the axis of view of the camera. The diffuse off-axis light source can comprise a rim that can be adapted to substantially prevent light rays from the diffuse off-axis light source from directly illuminating the surface of the object;

a set of medium angle direct light sources attached to the dome that can direct light rays directly upon the surface of the object. Slots in the dome can permit passage of and direct the light rays. An angle of the light rays from the medium angle direct light sources relative to the plane that is substantially perpendicular to the axis of view of the camera can be approximately 45 degrees; and/or a set of low angle direct light sources attached to the dome that can direct light rays directly upon the surface of the object. Slots in the dome can permit passage of and/or direct the light rays. An angle of light rays from the low angle direct light sources relative to the plane that is substantially perpendicular to the axis of view of the camera can be approximately 30 degrees.

Each of the set of light sources can be located at a predetermined distance and at a predetermined orientation relative to the field of view of the camera. The system can comprise one or more standoffs and/or a stand that position the system at a predetermined location relative to the object. The system can comprise a light zone controller that, based upon information obtained via the camera, can automatically determine a predetermined subset of the set of controlled light sources that are used to illuminate the object. The light zone controller can cause the subset of controlled light sources to illuminate the surface of the object.

FIG. 1 is a perspective view of an exemplary embodiment of a system 1000, which can be a self-contained imaging system. System 1000 can comprise an imaging module 1100, a stand 1200, a pedestal 1300, an information device 1400 and a memory device 1500. Imaging module 1100 can be a machine vision imaging module. Imaging module 1100 can be mechanically coupled to stand 1200, thereby semi-fixedly positioning imaging module 1100 at a predetermined location relative to pedestal 1300. Stand 1200 can be adapted to slideably change a distance of imaging module 1100 from pedestal 1300. A distance between imaging module 1100 and pedestal 1300 can be established based upon a size and/or type of marking on the object. Pedestal 1300 can define a plane that is substantially perpendicular to an axis of view of a camera comprised by imaging module 1100.

An object can be placed on pedestal 1300 within a field of view of the camera of imaging module 1100. Imaging module 1100 can be adapted to obtain image information regarding the object. With imaging module 1100 mounted to stand 1200, with adjustment of the distance between imaging module 1100 and pedestal 1300, imaging information can be obtained regarding parts of varying thicknesses.

Imaging module 1100 can be communicatively coupled to information device 1400. In certain exemplary embodiments, information device 1400 can be intrinsic and/or integral to imaging module 1100. In such embodiments, heat can be transferred from information device 1400 via an aperture and/or housing comprised by imaging module 1100. Information device 1400 can be adapted to receive information from the camera and/or can be adapted to control illumination of a set of light sources comprised by imaging module 1100. For example, a first subset of the set of light sources can be automatically illuminated via information device 1400. The camera of imaging module 1100 can obtain image information of an object and provide the image information to information device 1400. Information device 1400 can be adapted to interpret the image information and automatically illuminate a second subset of the set of light sources in order to attempt to obtain improved image information regarding the object. Information device 1400 can be adapted to iteratively change subsets of the set of light sources until the image information is deemed by information device 1400 to provide desired information (e.g., bar code information). Information device 1400 can be a machine vision information device adapted to interpret an image obtained via the camera of imaging module 1100. Information device 1400 can be adapted to store the image information in memory device 1500.

Figure 2:
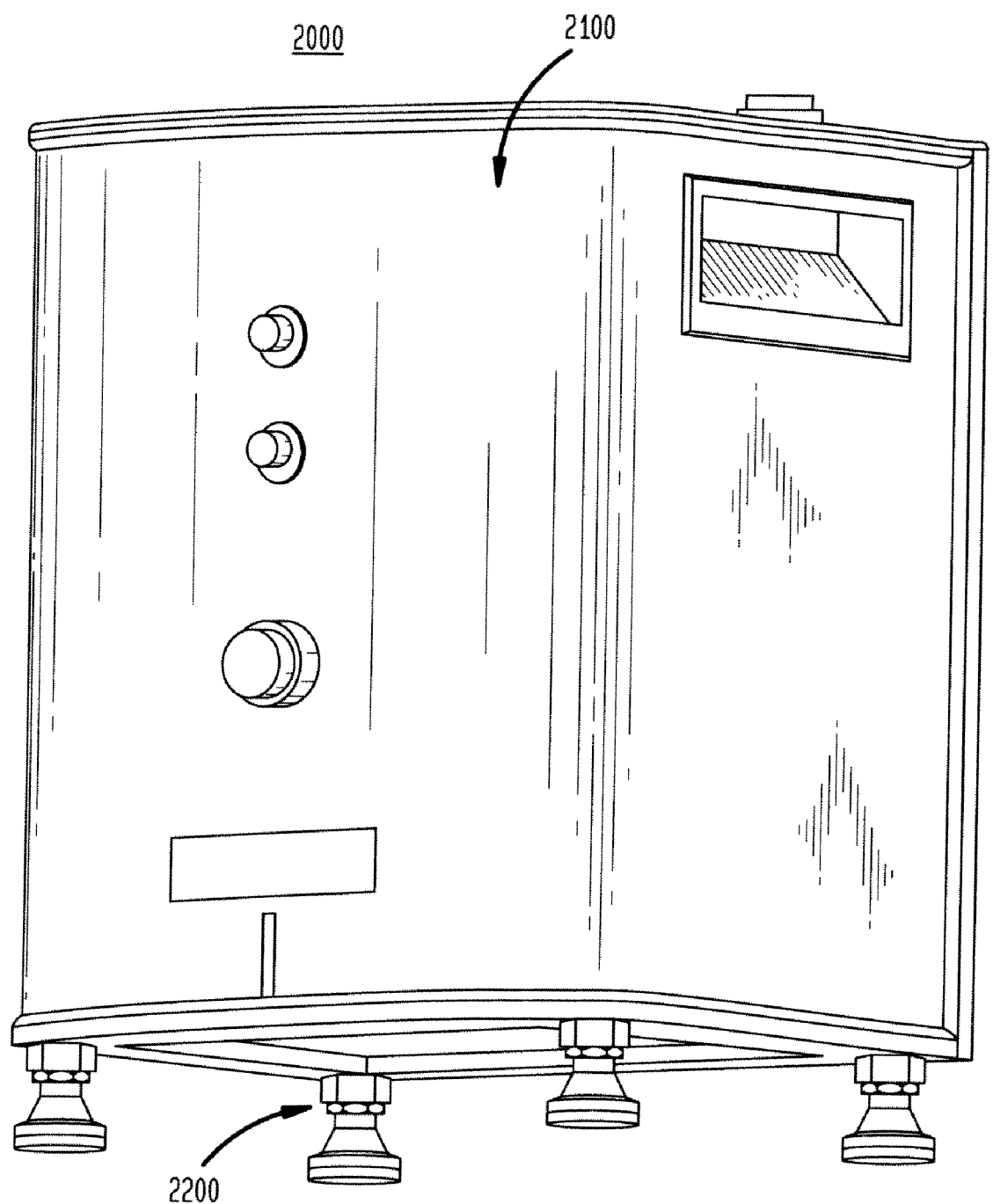
FIG. 2 is a perspective view of an exemplary embodiment of a system 2000.

FIG. 2 is a perspective view of an exemplary embodiment of a system 2000, which can comprise an imaging module 2100. In certain exemplary embodiments, imaging module 2100 can comprise a set of standoffs 2200, such as the four standoffs illustrated in system 2000. A count of standoffs can be any number that functions to support system 2000 relative to an object viewed thereby. For example the count of standoffs can be 3, 4, 5, 6, 7, 8, etc. Standoff 2200 can allow imaging module 2100 to be rested and/or pressed against a fixed object or surface. A height of set of standoffs 2200 can maintain a distance from the camera to the object. Standoffs 2200 can be adapted to contact a surface upon which system 2000 is operatively placed and position system 2000 at a predetermined location relative to the object.

Figure 3:
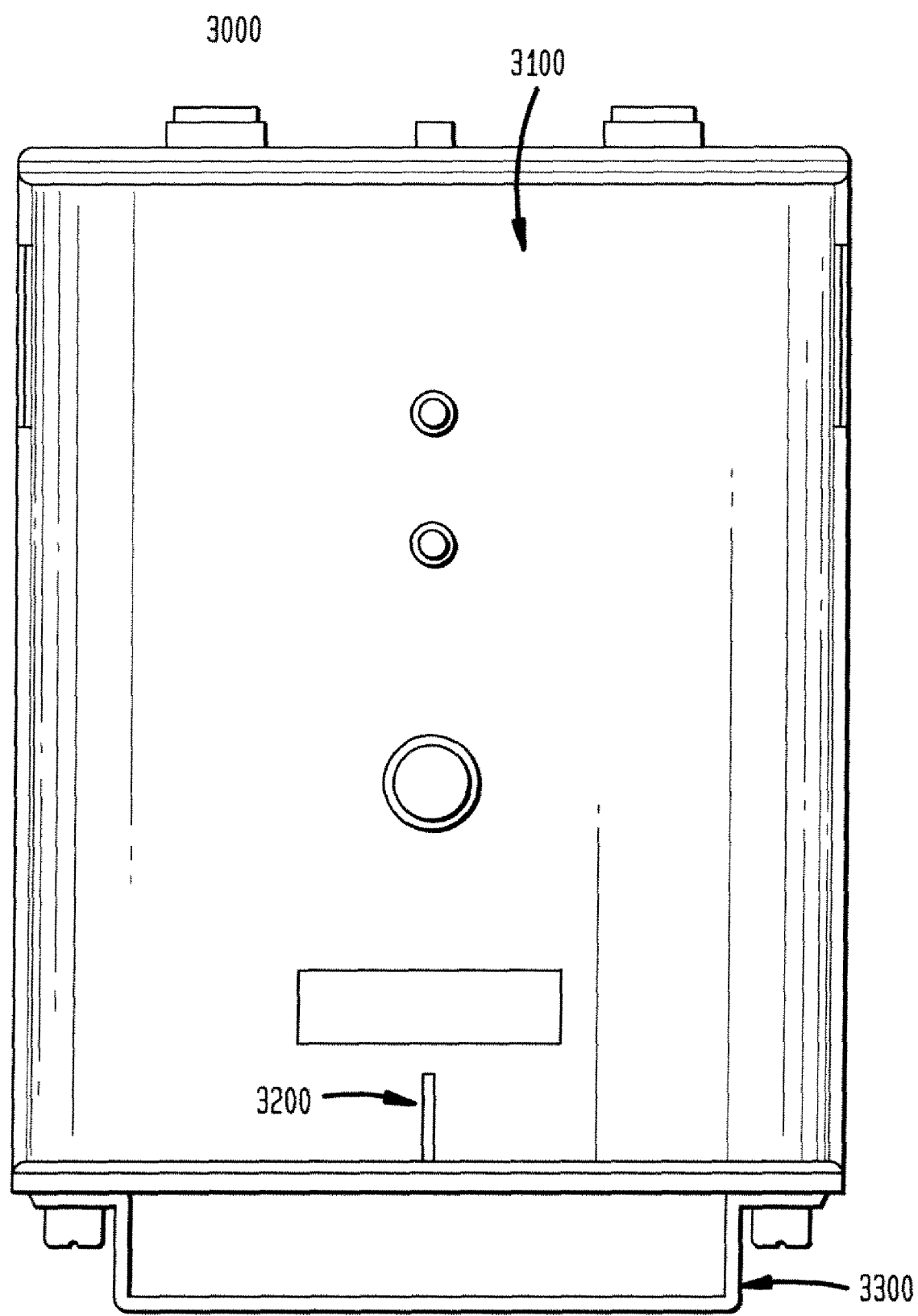
FIG. 3 is a side view of an exemplary embodiment of a system 3000.

FIG. 3 is a side view of an exemplary embodiment of a system 3000, which can comprise an imaging module 3100, a set of vertical marks 3200, and a presentation accessory 3300. Certain exemplary embodiments can comprise various standoff and presentation accessories and/or indicators such as:

set of vertical marks 3200 on one or more sides of imaging module 3100 to aid a user in manually positioning an object near a center of a field of view of a camera comprised by imaging module 3100; and/or a presentation accessory with viewing aperture, which can maintain a working distance from the camera to the object, etc.

Figure 4:
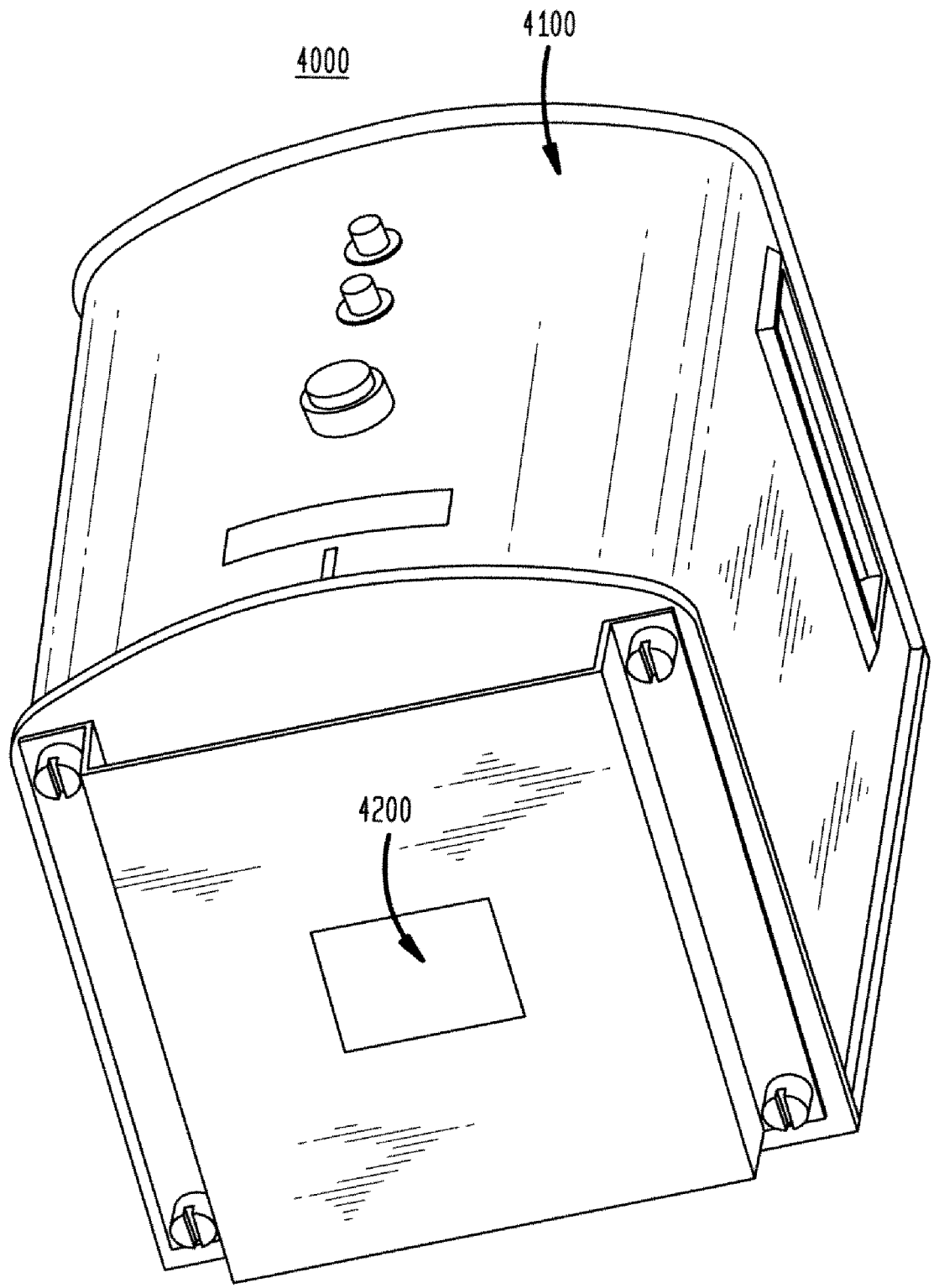
FIG. 4 is a perspective view of an exemplary embodiment of a system 4000.

FIG. 4 is a perspective view of an exemplary embodiment of a system 4000, which can comprise an imaging module 4100. Imaging module 4100 can define an aperture 4200, which can allow a camera comprised by imaging module 4100 to view an object.

Figure 5:
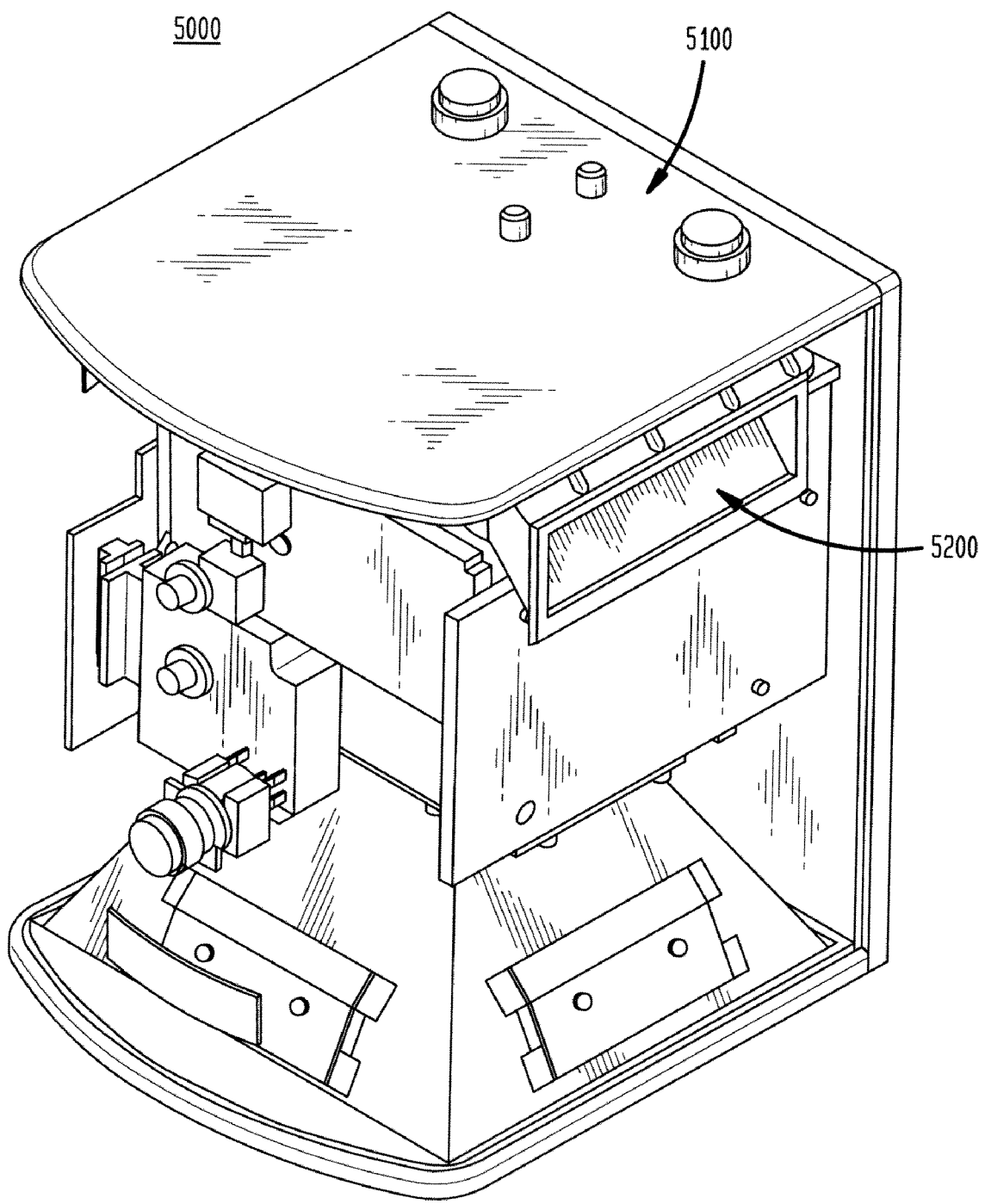
FIG. 5 is a perspective view of an exemplary embodiment of a system 5000.

FIG. 5 is a perspective view of an exemplary embodiment of a system 5000, which can comprise an imaging module 5100. In certain exemplary embodiments, imaging module 5100 can define an opening 5200. Opening 5200 can function as a handle for lifting, positioning, and/or relocating imaging module 5100. In certain exemplary embodiments, imaging module 5100 can be a self contained unit that comprises unit identifier compliant lighting, a camera, a lens, a light zone controller board, a camera power supply board, one or more image acquire triggers, and/or light emitting diode status indicators, etc.

Figure 6:
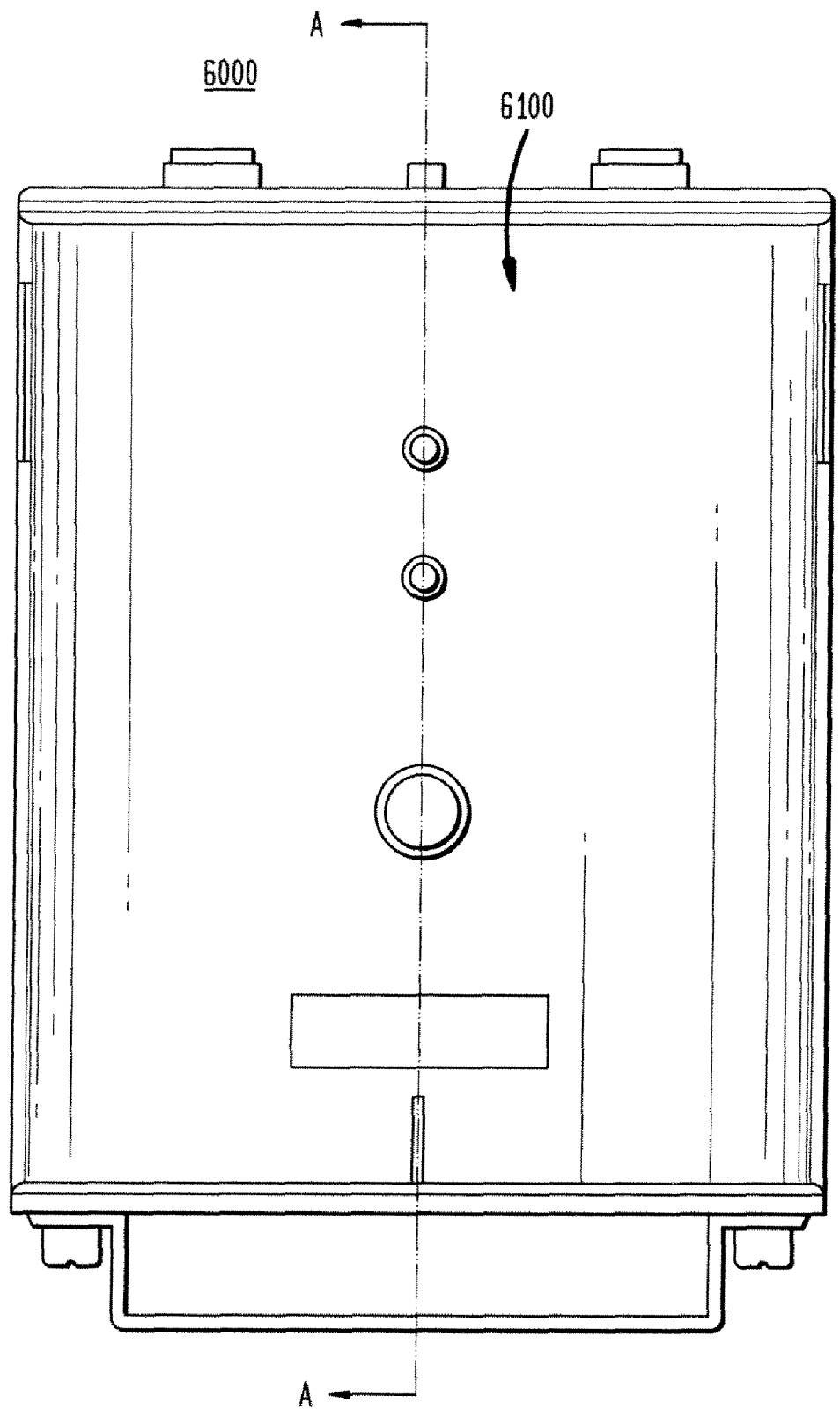
FIG. 6 is a side view of an exemplary embodiment of a system 6000.

FIG. 6 is a side view of an exemplary embodiment of a system 6000, which can comprise an imaging module 6100. A section A-A taken of system 6000 is presented as FIG. 7.

Figure 7:
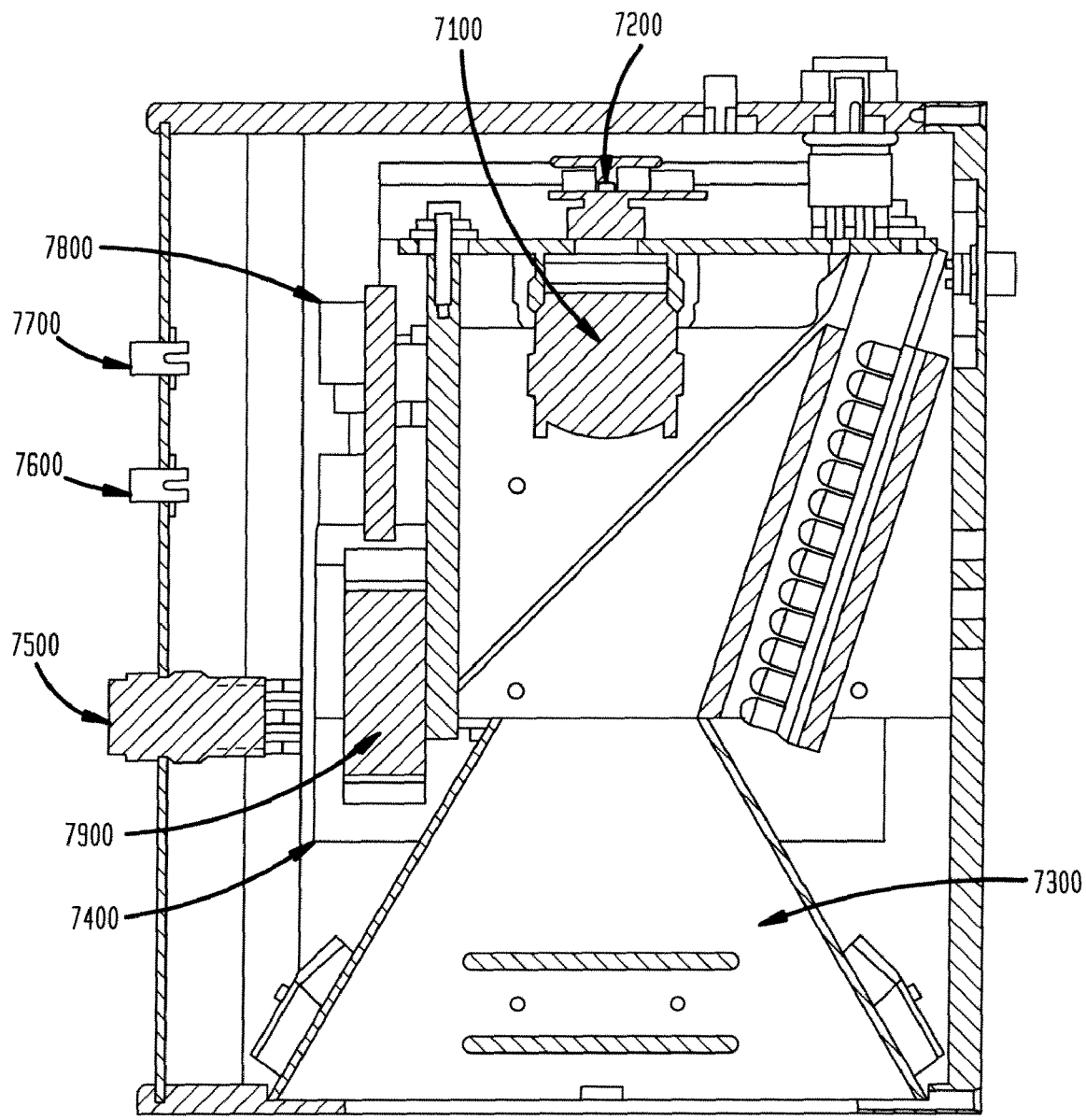
FIG. 7 is a sectional view of system 6000.

FIG. 7 is a sectional view of system 6000, which can comprise a camera lens 7100, a camera 7200, a lighting attachment 7300, a light controller 7400, an image acquire trigger 7500, a first light emitting diode (LED) read indicator 7600, a second LED read indicator 7700, and/or a camera power supply 7800. In certain exemplary embodiments, system 6000 can comprise:
- multiple lighting geometries;
- camera 7200;
- lens 7100;
- light controller 7400 (that can accept commands from camera 7200 and/or turn on or off one or more light sources);
- camera input/output (I/O) board 7900, which can be a circuit board adapted to transmit inputs and outputs between camera 7200 and a device external to camera 7200;
- camera power supply 7800, which can be a circuit board adapted to provide electrical energy to camera 7200;
- image acquire triggers (e.g., pushbuttons);
- LED indicators 7500 and 7600, which can indicate a pass vs. fail status of an image acquisition; and/or
- one or more pull handles for portability.

Light controller 7400 can be adapted to, responsive to information obtained via camera 7200, automatically illuminate at least one of the plurality of light sources to illuminate the object.

Figure 8:
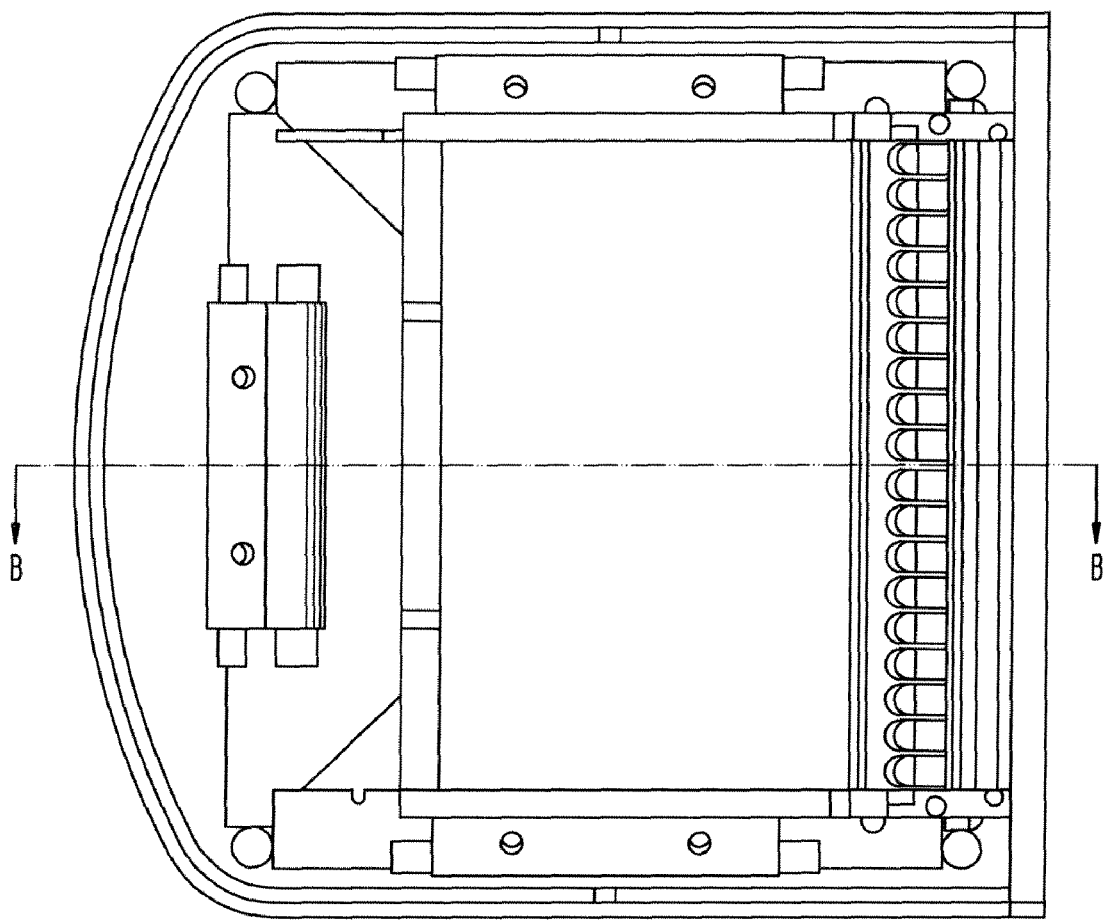
FIG. 8 is a plan view of an exemplary embodiment of a system 8000.
Figure 9:
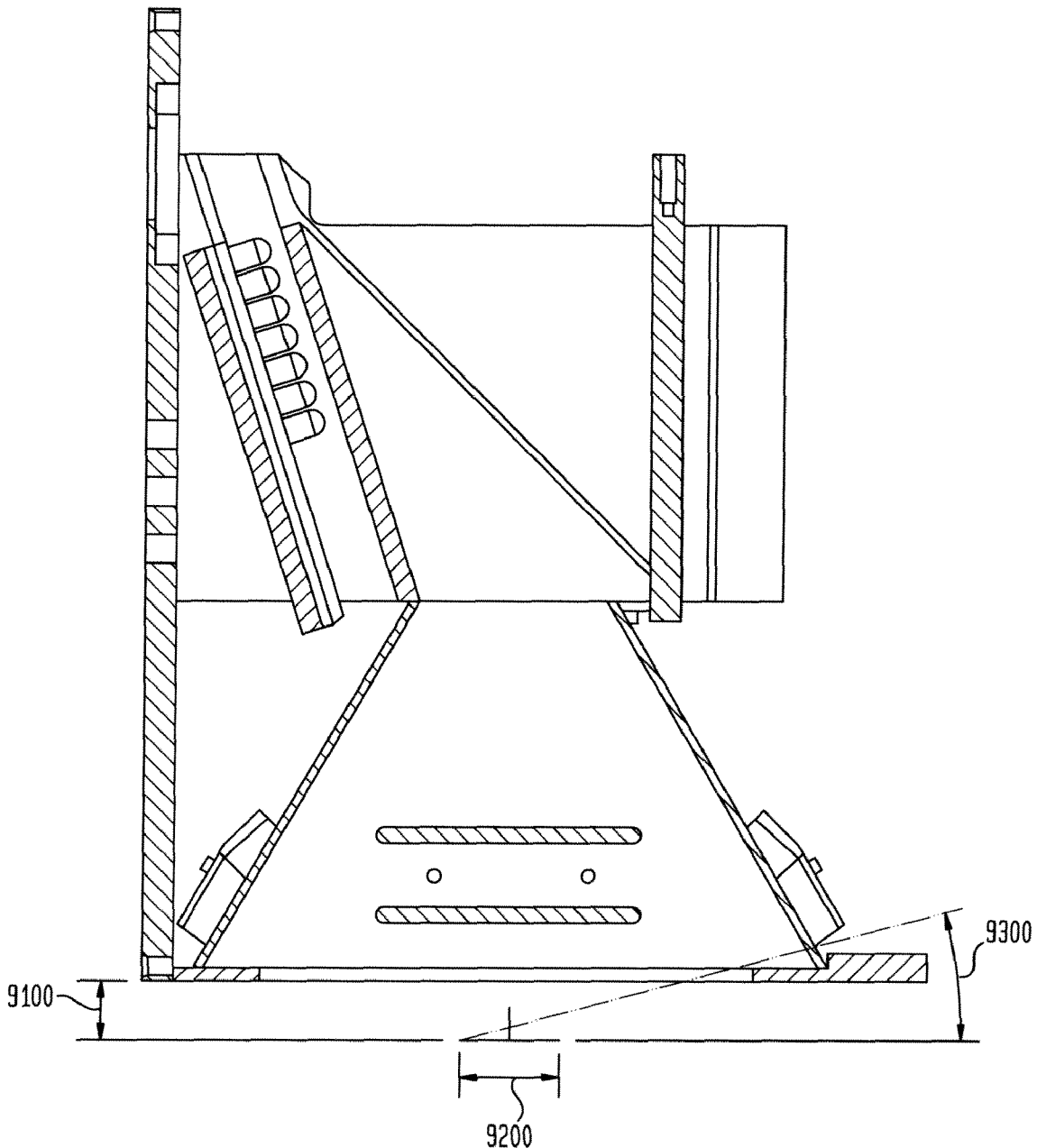
FIG. 9 is a sectional view of system 8000.

FIG. 8 is a plan view of an exemplary embodiment of a system 8000, from which a sectional view B-B of FIG. 9 can be derived.

FIG. 9 is a sectional view of system 8000, which can define geometric features of system 8000. System 8000 can define a distance 9100 between an exemplary imaging module and a plane upon which an object can be placed for viewing by system 8000. Distance 9100 can be based upon characteristics of a camera of system 8000. For example, distance 9100 can be approximately, in inches, 0.1, 0.32, 0.49, 0.5, 0.64, 0.73, 0.89, 0.97, 1, 1.15, 1.25, 1.36, etc., and/or any value or subrange therebetween. A field of view 9200 of the camera of system 8000 can be based upon characteristics of a camera of system 8000. For example, field of view 9200 can be approximately, in inches, 0.08, 0.26, 0.34, 0.4, 0.66, 0.78, 0.91, 1.07, 1.22, 1.35, 1.46, 1.57, etc., and/or any value or subrange therebetween. A set of low angle direct lighting sources of system 8000 can define an angle 9300 between light rays emitted by the set of low angle direct lighting sources and a plane perpendicular to a viewing axis of the camera of system 8000. In certain exemplary embodiments, angle 9300 can be approximately, in degrees, 11, 13, 16, 22, 24, 29, 30, 36, etc., and/or any value or subrange therebetween.

Figure 10:
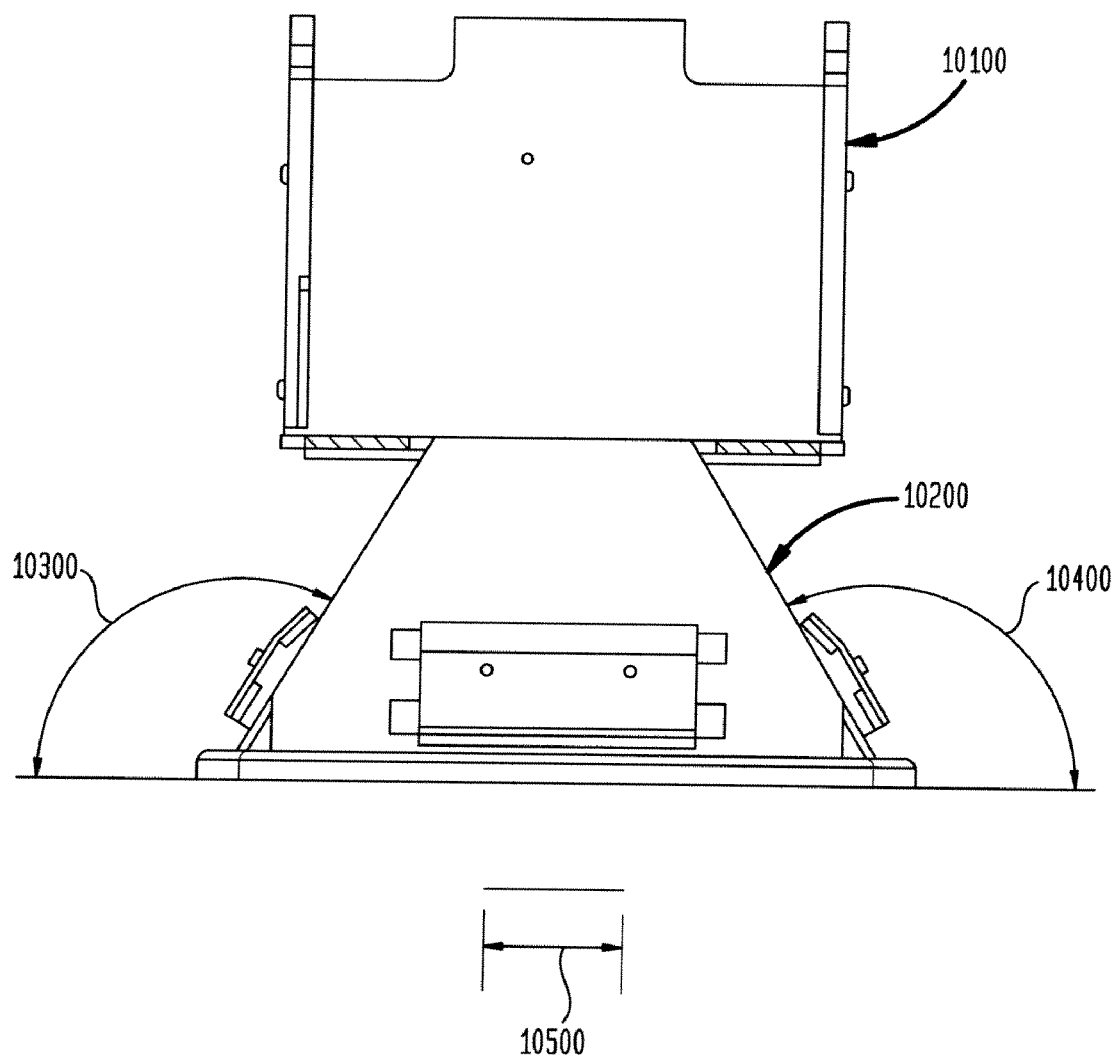
FIG. 10 is a side view of an exemplary embodiment of a system 10000.

FIG. 10 is a side view of an exemplary embodiment of a system 10000, which can comprise a crown 10100 and a dome 10200. Crown 10100 can be operatively coupled to dome 10200. Dome 10200 can define a first angle 10300 and a second angle 10400 relative to a plane that is substantially perpendicular to an axis of view of a camera comprised by system 10000. In certain exemplary embodiments, first angle 10300 and/or second angle 10400 can be approximately, in degrees, 105, 113, 116, 120, 124, 129, 130, 145, etc., and/or any value or subrange therebetween. A field of view 10500 of the camera of system 10000 can be based upon characteristics of a camera of system 10000. For example, field of view 10500 can be approximately, in inches, 0.15, 0.22, 0.34, 0.49, 0.61, 0.88, 0.99, 1.07, 1.19, 1.32, 1.41, 1.75, etc., and/or any value or subrange therebetween.

Figure 11:
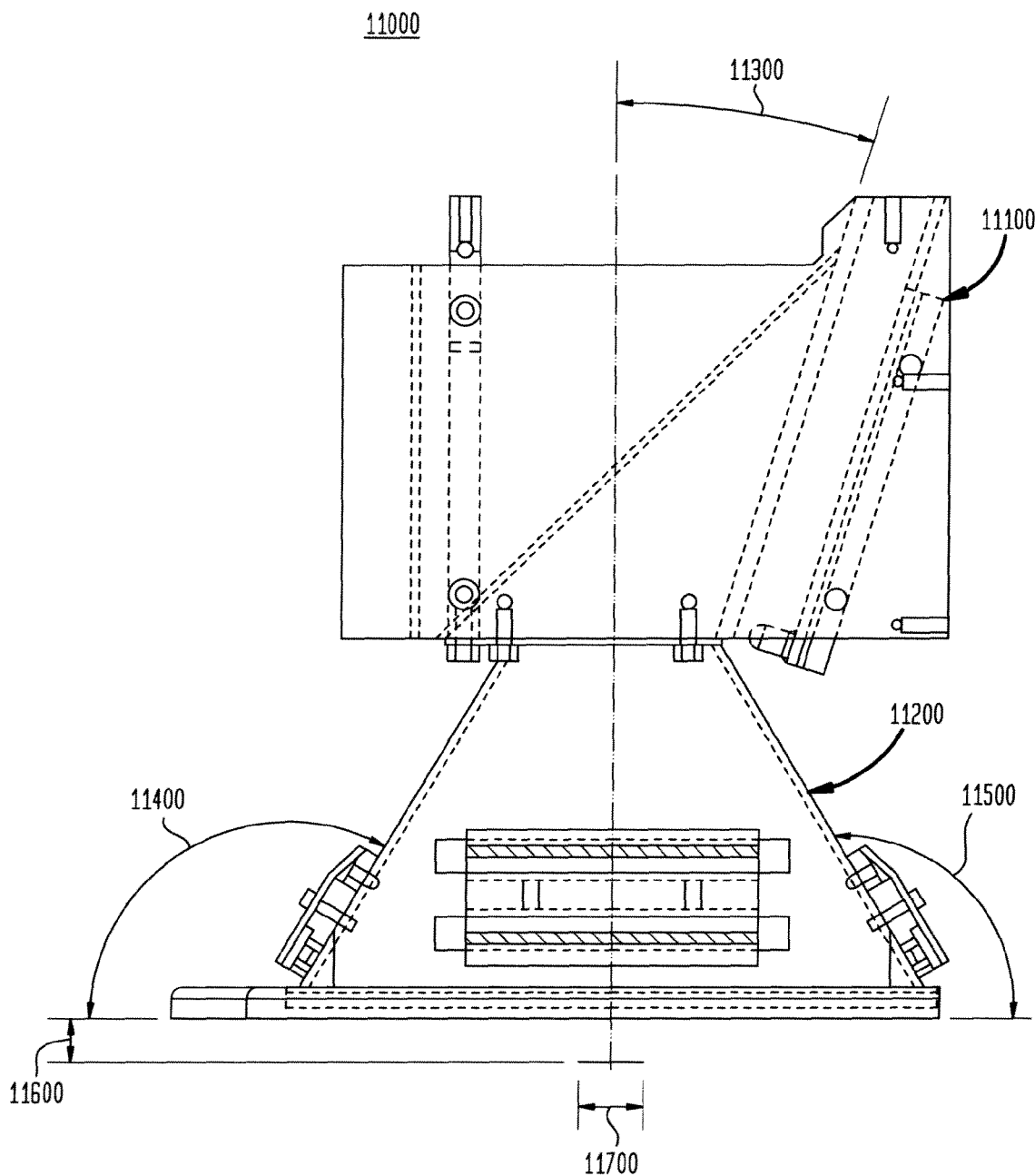
FIG. 11 is a side view of an exemplary embodiment of a system 11000.

FIG. 11 is a side view of an exemplary embodiment of a system 11000, which can comprise a crown 11100 and a dome 11200. Crown 11100 can be operatively coupled to dome 11200. Dome 11200 can define a first angle 11400 and a second angle 11500 relative to a plane that is substantially perpendicular to an axis of view of a camera comprised by system 11000. In certain exemplary embodiments, first angle 11400 and/or second angle 11500 can be approximately, in degrees, 100, 111, 120, 128, 135, 141, 150, etc., and/or any value or subrange therebetween. A field of view 11700 of the camera of system 11000 can be based upon characteristics of a camera of system 11000. For example, field of view 10500 can be approximately, in inches, 0.10, 0.18, 0.30, 0.41, 0.66, 0.78, 0.91, 1.0, 1.13, 1.24, 1.3, 1.5, etc., and/or any value or subrange therebetween. System 11000 can define a distance 11600 between an exemplary imaging module and a plane upon which an object can be viewed. Distance 11600 can be based upon characteristics of a camera of system 11000. For example, distance 11600 can be approximately, in inches, 0.1, 0.245, 0.5, 0.61, 0.69, 0.75, 0.89, 0.923, 1, 1.06, 1.21, 1.37, etc., and/or any value or subrange therebetween.

Figure 12:
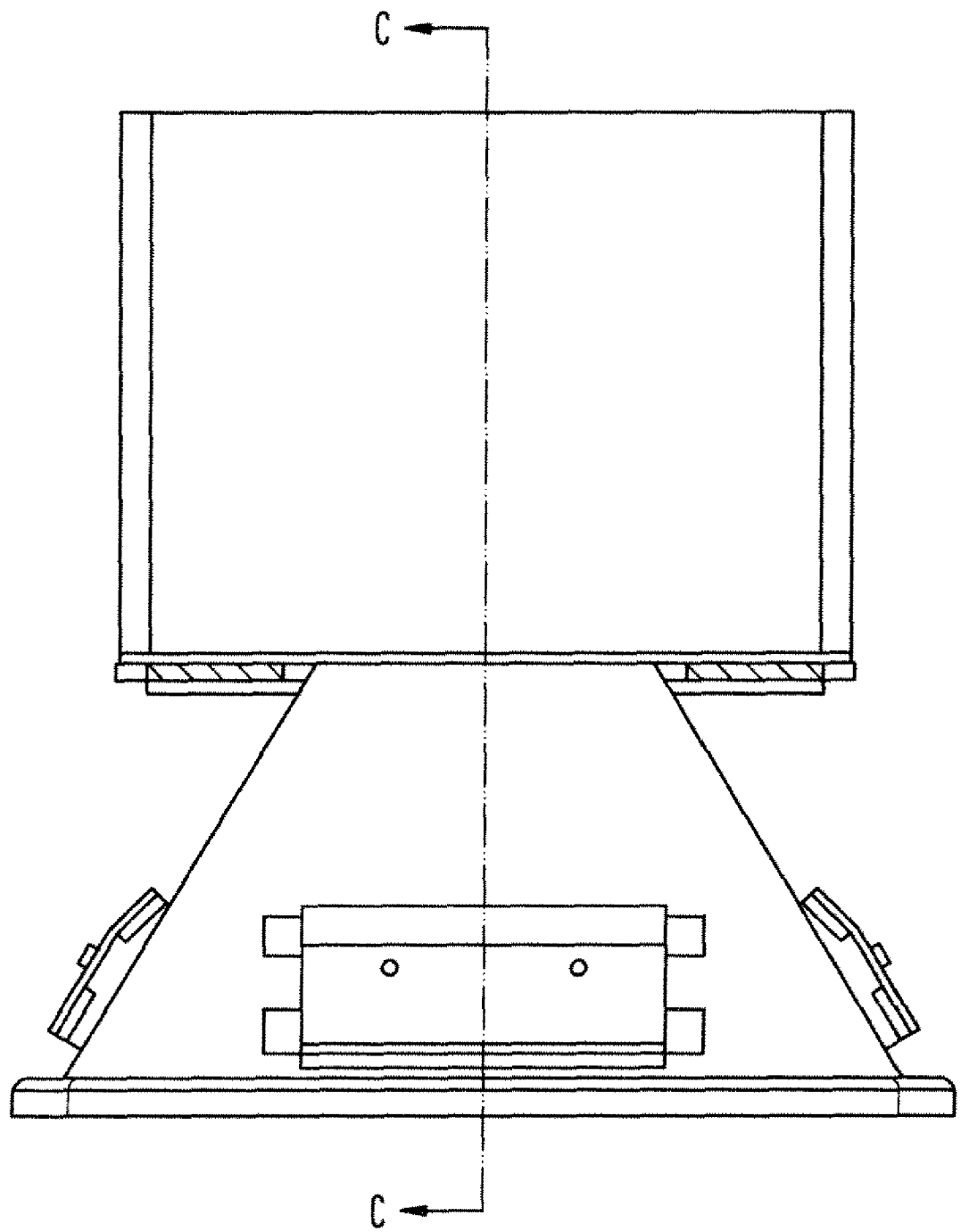
FIG. 12 is a side view of an exemplary embodiment of a system 12000.

FIG. 12 is a side view of an exemplary embodiment of a system 12000 from which a sectional view C-C can be derived.

Figure 13:
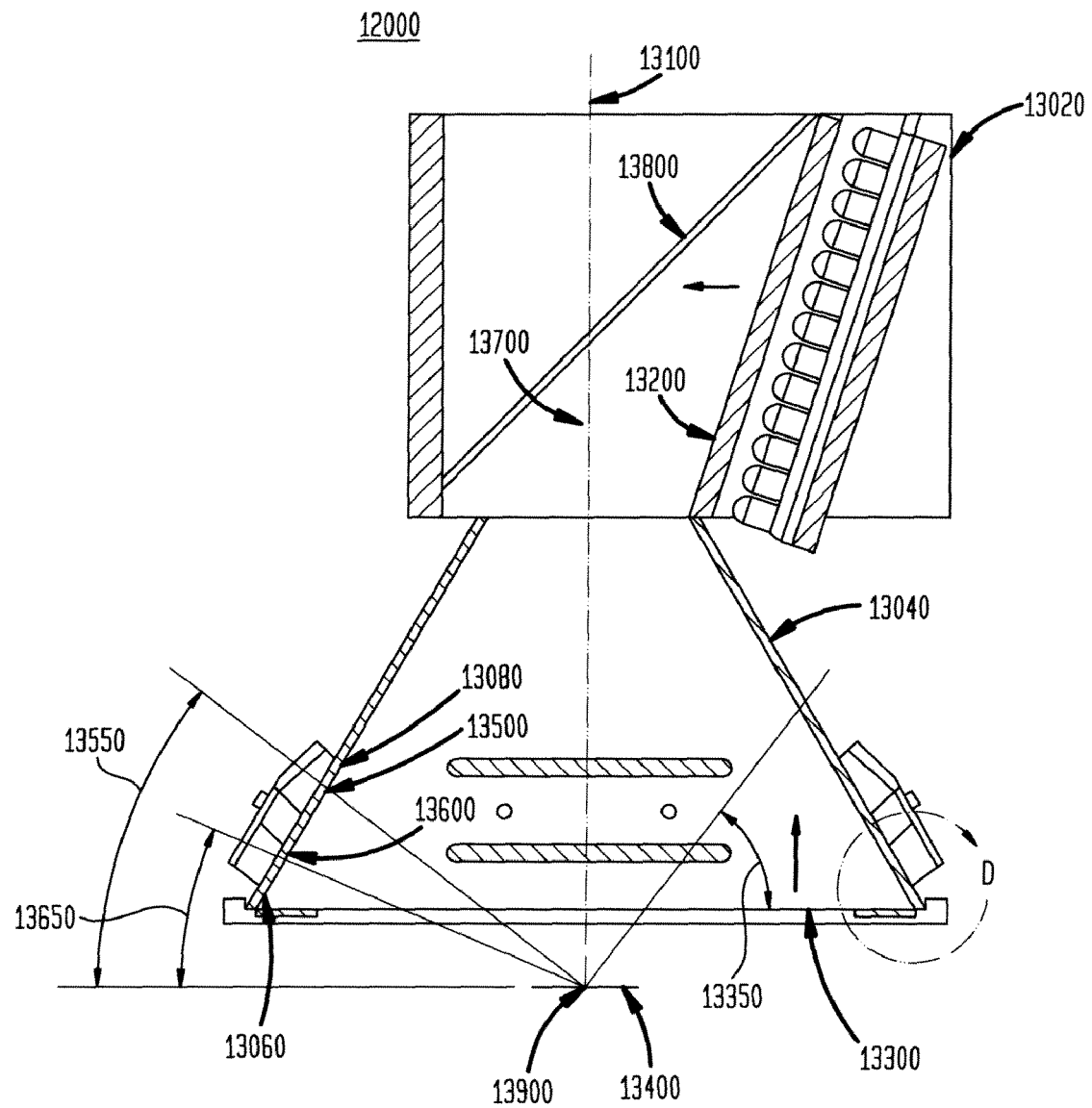
FIG. 13 is a sectional view of system 12000.

FIG. 13 is a sectional view of system 12000 that corresponds to section C-C of FIG. 12. System 12000 can comprise a crown 13020, a dome 13040, and a beamsplitter 13800. Dome 13040 can have a truncated four-sided pyramid shape. Crown 13020 can be adapted to be operatively coupled to an apex portion of dome 13040.

System 12000 can define a viewing axis 13100 and a plane 13400, which is substantially perpendicular to viewing axis 13100. System 12000 can comprise a plurality of light sources adapted to illuminate an object 13900. Each of the plurality of light sources can be located at a predetermined distance and a predetermined orientation relative to a viewing plane 13400 of a camera adapted to be supported by dome 13040 and adapted to obtain an image of the illuminated object 13900. Viewing plane 13400 can be substantially perpendicular to viewing axis 13100 of the camera. In certain exemplary embodiments, system 12000 can comprise lighting sources adapted to illuminate object 13900, which can comprise:
- a set of diffuse perpendicular (on-axis, brightfield, 90) light sources 13200;
- a set of diffuse off-axis (dome) light sources 13300;
- a set of low angle, four direction (30Q), light sources 13600;
- a set of low angle, two direction (30T), light sources 13600;
- a set of low angle, one direction (30S, light is aimed at the part from any of the four sides) light sources 13600; and/or
- a set of low angle, four direction (45Q) light sources 13500.

The lighting sources of system 12000 can comprise set of low angle direct light sources 13600 operatively coupled to dome 13040. Low angle direct light sources 13600 can be adapted to illuminate object 13900 via a set of apertures 13060 defined by dome 13040. Set of apertures 13060 can be adapted to cause light rays from low angle direct light sources 13600 to intersect viewing plane 13400 at an angle 13650 of approximately 30 degrees.

The lighting sources of system 12000 can comprise set of medium angle direct light sources 13500 attached to dome 13040. Slots 13080 defined by dome 13040 can be adapted to cause light rays from medium angle direct light sources 13500 to intersect viewing plane 13400 at an angle 13550 of approximately 45 degrees.

The lighting sources of system 12000 can comprise a set of light sources 13300 that is directed toward dome 13040. A count of lights in set of light sources 13300 can be any number such as, 1, 2, 3, 4, 5, 6, 7, 8, etc. Dome 13040 can be adapted to reflect light rays from light source 13300 toward viewing plane 13400 at an angle 13350 with respect to viewing plane 13400 of between approximately 45 degrees and approximately 90 degrees.

The lighting sources of system 12000 can comprise diffuse on-axis light source 13200 from the plurality of light sources. Diffuse on-axis light source 13200 can be coupled to crown 13020 and directed toward beamsplitter 13800. Beamsplitter 13800 can be adapted to reflect a portion of light rays 13700 from diffuse on-axis light source 13200 at an angle that is approximately perpendicular to viewing plane 13400 and approximately parallel to viewing axis 13100.

In certain exemplary embodiments, each light source can be embodied as an LED light source, which can emit light at wavelengths of approximately 640 nanometers. Exemplary embodiments can incorporate LED light sources from a visible range up to a near infrared range. A detail D can be derived from FIG. 13.

Figure 14:
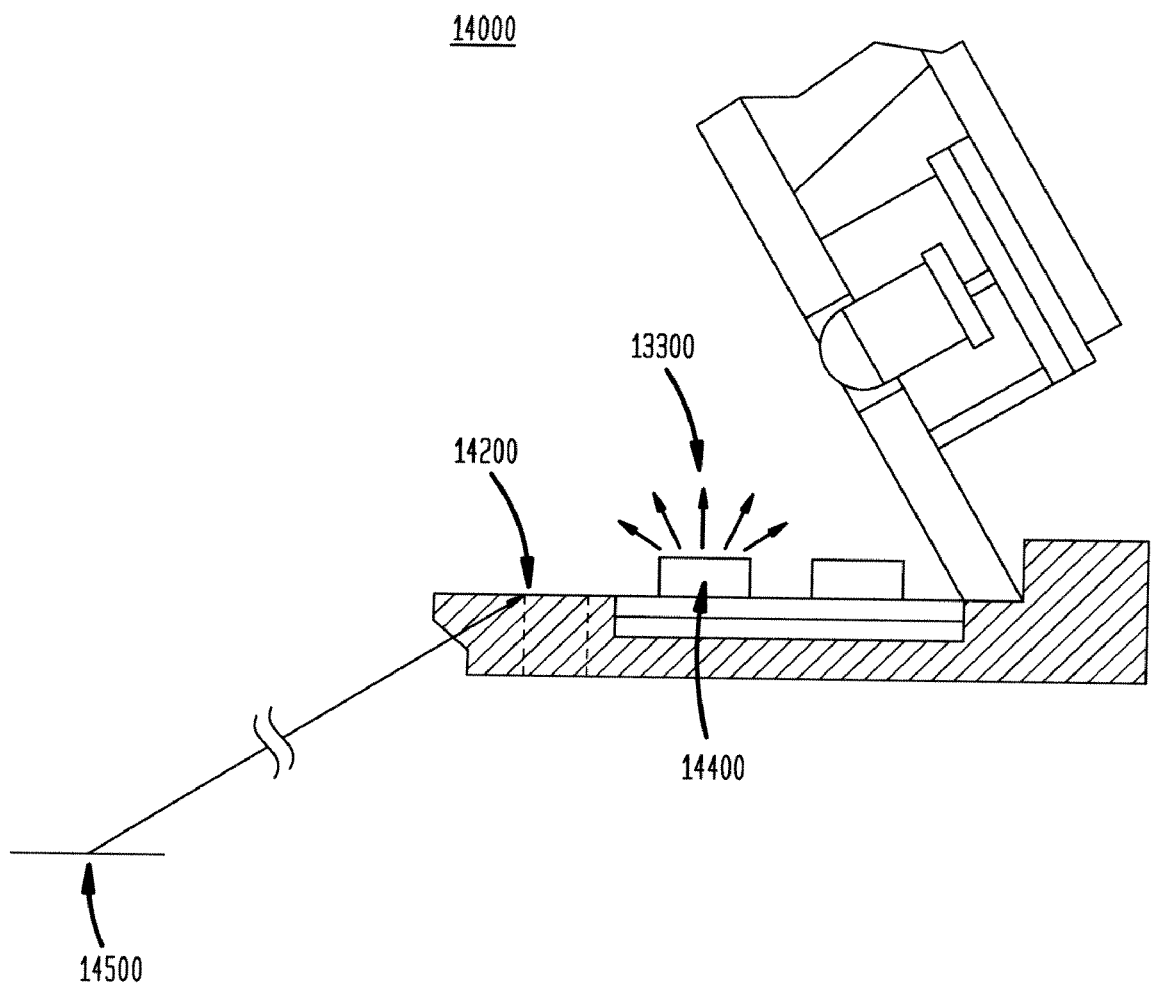
FIG. 14 is a detail view of a portion 14000 of system 12000.

FIG. 14 is a detail view of a portion 14000 of system 12000 that is partially derived from detail D of FIG. 13. Portion 14000 of system 12000 can comprise a dome light source 13300, which can comprise a light 14400 (e.g., an LED) and a rim 14200. Rim 14200 can act as a baffle and substantially prevents rays from light 14400 from directly reaching a field of view 14500 of portion 14000 of system 12000 and/or directly illuminating the object.

Figure 15:
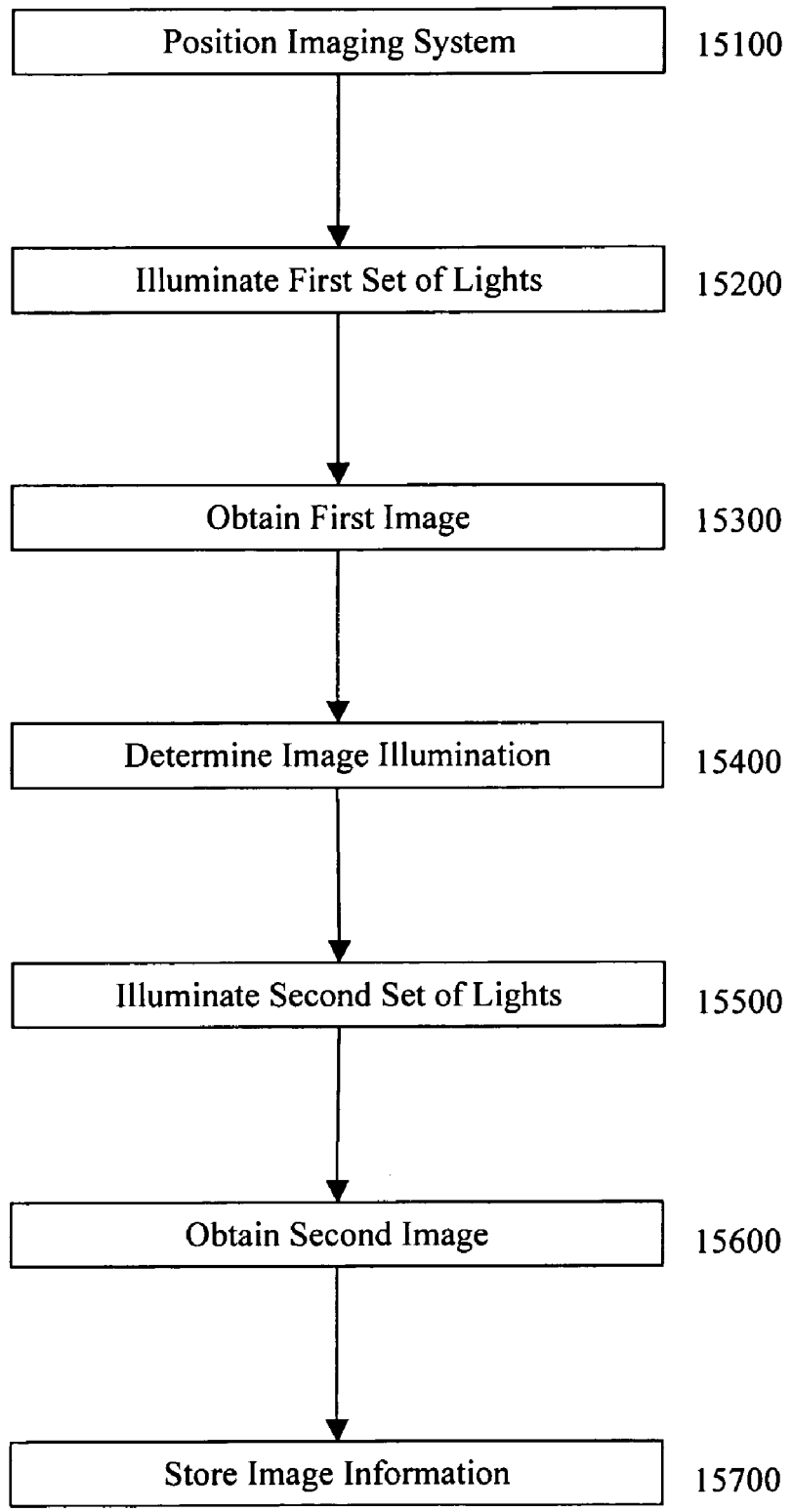
FIG. 15 is a flowchart of an exemplary embodiment of a method 15000.

FIG. 15 is a flowchart of an exemplary embodiment of a method 15000. In certain exemplary embodiments, one or more activities of method 15000 can be carried out automatically via an information device. Machine-implementable instructions embodying one or more activities of method 15000 can be stored in a memory and can be executed by a processor of the information device. At activity 15100, an imaging system can be positioned relative to an object to be viewed by the imaging system.

At activity 15200, a first set of light sources of the imaging system can be illuminated. In certain exemplary embodiments, a light controller, responsive to information obtained via a camera of the imaging system, can be adapted to cause an automatic illumination of at least one of a plurality of light sources. Each of the plurality of light sources can be adapted to illuminate an object in a field of view of the camera. Each of the plurality of light sources can be located at a predetermined distance and a predetermined orientation relative to a viewing plane of the camera. The camera can be adapted to be supported by a dome and adapted to obtain an image of the illuminated object. The dome can have a truncated four-sided pyramid shape. The viewing plane can be substantially perpendicular to a viewing axis of the camera. The plurality of light sources can comprise:

a set of low angle direct light sources operatively coupled to the dome, the low angle direct light sources can be adapted to illuminate the object via a set of apertures defined by the dome, the set of apertures adapted to cause light rays from the low angle direct light sources to intersect the viewing plane at an angle of approximately 30 degrees;

a set of medium angle direct light sources attached to the dome, slots defined by the dome adapted to direct light rays from the medium angle direct light sources, an angle defined by the light rays from the medium angle direct light sources and the plane approximately 45 degrees;

a light source that is directed toward the dome, the dome adapted to reflect light rays from the light source toward the viewing plane at an angle with respect to the viewing plane of between approximately 45 degrees and approximately 90 degrees, the light source comprising a rim that prevents light rays from the light source directed toward the dome from directly illuminating the object; and/or a diffuse on-axis light source from the plurality of light sources operatively coupled to a crown, the crown operatively coupled to the dome, the diffuse on-axis light source directed toward a beamsplitter, the beamsplitter adapted to reflect a portion of light rays from the diffuse on-axis light source at an angle that is approximately perpendicular to the viewing plane.

In certain exemplary embodiments, an illumination of the low angle direct light sources can be caused without illumination from additional light sources of the plurality of light sources. In certain exemplary embodiments, an illumination of each of the plurality of light sources can be caused to occur sequentially. In certain exemplary embodiments, an illumination of substantially all of the plurality of light sources can be caused to occur substantially simultaneously.

At activity 15300, a first image of the object can be obtained. The first image can be stored and/or transmitted to an information device. At activity 15400, the information device associated with the imaging system can determine whether illumination of the image was sufficient to deduce information from the image. For example, in embodiments where the first image comprises direct product mark (DPM) information, the information device can be adapted to attempt to resolve the DPM information from the first image.

At activity 15500, based upon an analysis performed by the information device, a second set of lights can be illuminated to improve illumination of the object. In certain exemplary embodiments, based upon the first image of the object, an automatic determination can be made of which of the plurality of light sources to illuminate to obtain a subsequent image of the object At activity 15600, a second image of the object can be obtained via the camera. The second image can be stored and/or transmitted to the information device. At activity 15700, the information device can analyze and/or interpret information associated with the second image. For example, in embodiments where the second image comprises direct product mark (DPM) information, the information device can be adapted to attempt to resolve the DPM information from the second image.

In certain exemplary embodiments, if the information from the image cannot be deduced, activities 15400 through 15700 can be repeated recursively until information can be deduced from the image (e.g., bar code information, DPM information, etc.) or until a predetermined set of conditions or met by which the information device can automatically determine that the information cannot be deduced from the object based upon a determined illumination of the object by the imaging system.

Figure 16:
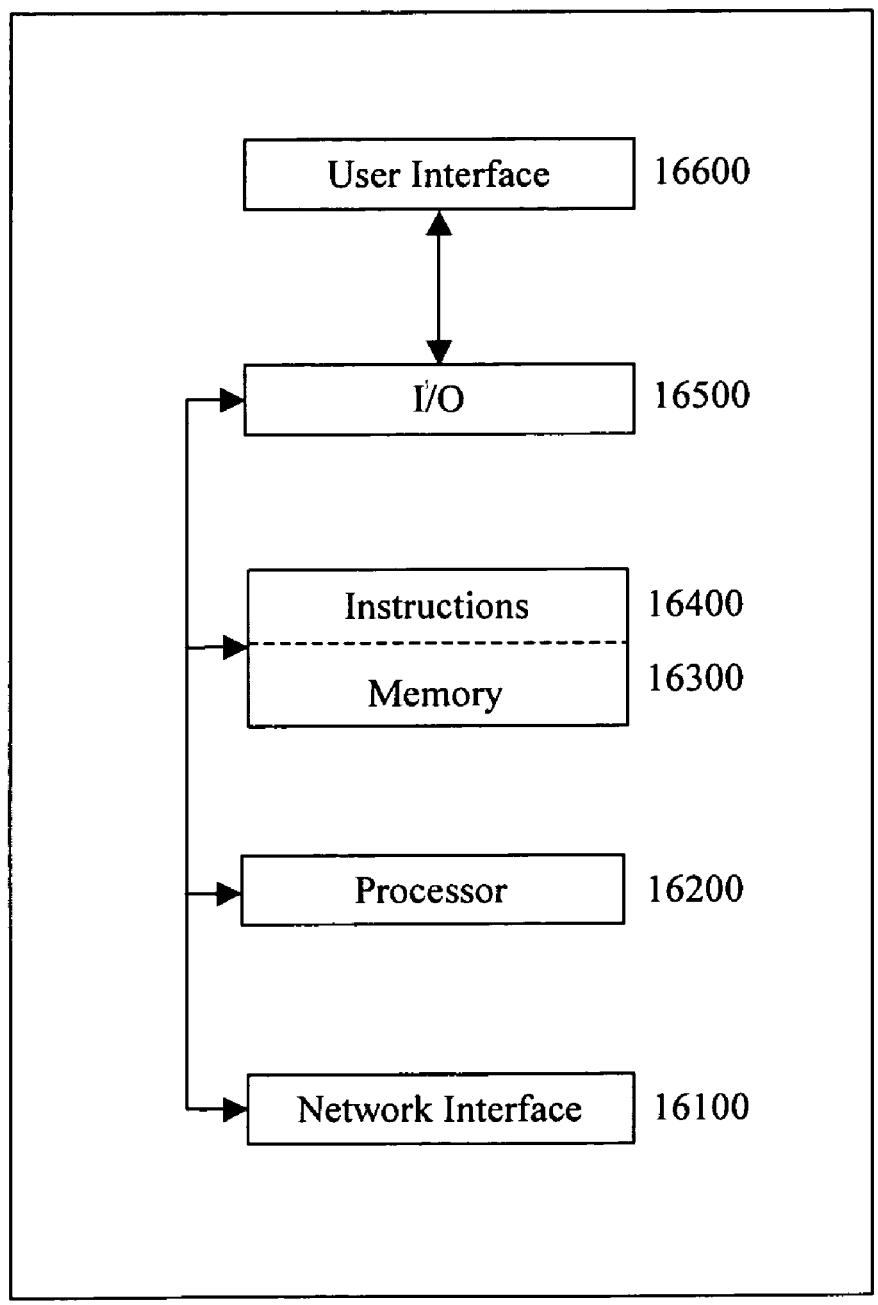
FIG. 16 is a block diagram of an exemplary embodiment of an information device 16000.

FIG. 16 is a block diagram of an exemplary embodiment of an information device 16000, which in certain operative embodiments can comprise, for example, information device 1400 of FIG. 1. Information device 16000 can comprise any of numerous circuits and/or components, such as for example, one or more network interfaces 16100, one or more processors 16200, one or more memories 16300 containing instructions 16400, one or more input/output (I/O) devices 16500, and/or one or more user interfaces 16600 coupled to I/O device 16500, etc.

In certain exemplary embodiments, via one or more user interfaces 16600, such as a graphical user interface, a user can view a rendering of information related to researching, designing, modeling, creating, developing, building, manufacturing, operating, maintaining, storing, marketing, selling, delivering, selecting, specifying, requesting, ordering, receiving, returning, rating, and/or recommending any of the products, services, methods, and/or information described herein.

DEFINITIONS

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

- a—at least one.
- activity—an action, act, deed, function, step, and/or process and/or a portion thereof.
- adapted to—suitable, fit, and/or capable of performing a specified function.
- additional—an act or process of adding.
- adjacent—in close proximity to, near, next to, and/or adjoining.
- and/or—either in conjunction with or in alternative to.
- aperture—an opening, hole, gap, passage, and/or slit.
- apex portion—a portion of a pyramid opposite the base.
- apparatus—an appliance or device for a particular purpose.
- approximately—about and/or nearly the same as.
- associated with—related to.
- at least—not less than.
- attach—to fasten, secure, couple, and/or join.
- automatically—acting and/or operating in a manner essentially independent of external human influence and/or control. For example, an automatic light switch can turn on upon "seeing" a person in its view, without the person manually operating the light switch.
- axis—a straight line about which a body or geometric object rotates or can be conceived to rotate and/or a center line to which parts of a structure or body can be referred.
- based upon—determined in consideration of and/or derived from.
- beamsplitter—a device and/or system adapted to of split and/or join a light beam into or from two or more beams that differ in wavelength, polarity, and/or direction.
- between—in a separating interval and/or intermediate to.
- camera—a device often comprising a lightproof enclosure having an aperture with a lens through which a still and/or moving image of an object is focused and recorded on a photosensitive film, plate, tape, and/or or sensor coupled to an electronic and/or optical memory device (e.g., RAM, EEPROM, flash memory, magnetic disk, optical disk, etc.).
- can—is capable of, in at least some embodiments.
- capable—a potential for use.
- capture—to obtain and/or record image data in preparation for processing and/or storage.
- cause—to bring about, provoke, precipitate, produce, elicit, be the reason for, result in, and/or effect.
- circuit—an electrically conductive pathway and/or a communications connection established across two or more switching devices comprised by a network and between corresponding end systems connected to, but not comprised by the network.
- circuit board—a wafer of material that is substantially electrically non-conductive on which electronic components are mounted and/or electrically coupled.
- component—a constituent element and/or part.
- comprised by—included by.
- comprise—to include but not be limited to.
- contact—to touch.
- control—to direct.
- controller—a device and/or set of machine-readable instructions for performing one or more predetermined and/or user-defined tasks. A controller can comprise any one or a combination of hardware, firmware, and/or software. A controller can utilize mechanical, pneumatic, hydraulic, electrical, magnetic, optical, informational, chemical, and/or biological principles, signals, and/or inputs to perform the task(s). In certain embodiments, a controller can act upon information by manipulating, analyzing, modifying, converting, transmitting the information for use by an executable procedure and/or an information device, and/or routing the information to an output device. A controller can be a central processing unit, a local controller, a remote controller, parallel controllers, and/or distributed controllers, etc. The controller can be a general-purpose microcontroller, such the Pentium IV series of microprocessor manufactured by the Intel Corporation of Santa Clara, Calif., and/or the HC08 series from Motorola of Schaumburg, Ill. In another embodiment, the controller can be an Application Specific Integrated Circuit (ASIC) or a Field Programmable Gate Array (FPGA) that has been designed to implement in its hardware and/or firmware at least a part of an embodiment disclosed herein.
- corresponding—related, associated, accompanying, similar in purpose and/or position, conforming in every respect, and/or equivalent and/or agreeing in amount, quantity, magnitude, quality, and/or degree.
- couple—to join, connect, and/or link two things together.
- crown—an upper portion of a camera system when a lens of an operatively mounted camera of the camera system is aimed in a substantially downward direction, this upper portion adapted to support the camera, to provide a mount for an on-axis light source, and/or to secure a beamsplitter.
- define—to establish the meaning, relationship, outline, form, and/or structure of, and/or to precisely and/or distinctly describe and/or specify.
- degree—a unit of measure of a plane angle representing 1/360 of a full rotation.
- design—(n) a purposeful arrangement of parts and/or details. For example, the design of a product and/or process can comprise designing predetermined aspects of the product and/or process. (v) to plan, such as in a manner that comprises the development of a graphic representation.
- determine—to obtain, calculate, decide, deduce, establish, and/or ascertain.
- device—a machine, manufacture, and/or collection thereof.
- diffuse on-axis light source—an illuminating device and/or system adapted to provide indirect illumination to a field of view of a camera via reflected light rays, the reflected light rays substantially parallel to a viewing axis of the camera.
- direct—to aim.
- distance—a measure of physical and/or logical separation.
- dome—a portion of a camera system having a concave shape and operatively coupled to a crown, the dome can be adapted to provide a mount for a set of low angle light sources, a set of medium angle light sources, and/or a light source adapted to reflect light rays from the dome. The dome can be painted white on the interior each—every one of a group considered individually.

electrical energy—energy characterized by the flow of electric charge through a conductor.

emit—to give off, send forth, and/or discharge.

external—relating to, existing on, and/or connected with the outside or an outer part; exterior.

field of view—a range of space over which a camera can obtain an image.

first—an initial entity in an ordering.

flow—a continuous transfer.

for—with a purpose of.

four-sided pyramid—a volume defined by four triangles that define a substantially square base; each base side of each of the four triangles forming a right angle with a base side of an adjacent triangle to form the square base, each non-base side of each triangle adjacent to and substantially co-linear with a non-base side of an adjacent triangle.

from—used to indicate a source.

further—in addition.

have—to be identified by.

illuminate—to light and/or cause light to be incident thereon.

image—an at least two-dimensional, observed representation of an entity and/or phenomenon.

indicator—one or more signs, tokens, symbols, signals, devices, and/or substance that indicates.

information—facts, terms, concepts, phrases, expressions, commands, numbers, characters, and/or symbols, etc., that are related to a subject. Sometimes used synonymously with data, and sometimes used to describe organized, transformed, and/or processed data. It is generally possible to automate certain activities involving the management, organization, storage, transformation, communication, and/or presentation of information.

information device—any device on which resides a finite state machine capable of implementing at least a portion of a method, structure, and/or or graphical user interface described herein. An information device can comprise well-known communicatively coupled components, such as one or more network interfaces, one or more processors, one or more memories containing instructions, one or more input/output (I/O) devices, and/or one or more user interfaces (e.g., coupled to an I/O device) via which information can be rendered to implement one or more functions described herein. For example, an information device can be any general purpose and/or special purpose computer, such as a personal computer, video game system (e.g., PlayStation, Nintendo Gameboy, X-Box, etc.), workstation, server, minicomputer, mainframe, supercomputer, computer terminal, laptop, wearable computer, and/or Personal Digital Assistant (PDA), iPod, mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, a digital signal processor, an ASIC or other integrated circuit, a hardware electronic logic circuit such as a discrete element circuit, and/or a programmable logic device such as a PLD, PLA, FPGA, or PAL, or the like, etc.

input—a signal, data, and/or information provided to a processor, device, and/or system.

instructions—directions adapted to perform a particular operation or function. Can be implemented as firmware and/or software.

interpret—to make sense of and/or assign a meaning to.

intersect—to cut across and/or through.

lens—a camera component that concentrates light and focuses an image.

light source—(n) a device and/or system adapted to provide illumination; (v) to provide electromagnetic radiation to which organs of sight react, ranging in wavelength from approximately 300 to approximately 1000 nm.

light controller—a controller that is adapted to cause an illumination of one or more light sources and/or provide intensity control of each light source.

light emitting diode (LED)—a semiconductor device that emits (typically visible) light responsive to an applied electrical conducting current.

located—situated in a particular spot and/or position.

location—a place.

low angle direct light sources—a group of illumination devices adapted to transmit light rays that directly illuminate an object at an angle less than 35 degrees relative to a viewing plane of an imaging device.

machine-implementable instructions—directions adapted to cause a machine, such as an information device, to perform one or more particular activities, operations, and/or functions. The directions, which can sometimes form an entity called a "processor", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.

machine-readable—capable of being discerned by an information device.

machine-readable medium—a physical structure from which a machine, such as an information device, computer, microprocessor, and/or controller, etc., can obtain and/or store data, information, and/or instructions. Examples include memories, punch cards, and/or optically-readable forms, etc.

machine vision—devices and/or systems adapted to use video cameras, robots, other devices, and/or computers to obtain and/or analyze visual and/or video information pertaining to an operation or activity.

may—is allowed and/or permitted to, in at least some embodiments.

medium angle direct light sources—a group of illumination devices adapted to transmit light rays directly illuminate an object at an angle between 30 degrees and 75 degrees relative to a viewing plane of an imaging device.

method—a process, procedure, and/or collection of related activities for accomplishing something.

object—a physical thing.

obtain—to receive, get, take possession of, procure, acquire, calculate, determine, and/or compute.

operative—being in effect; operating.

orientation—position a relative to a reference object.

output—(n) something produced and/or generated; data produced by an information device executing machine-readable instructions; and/or the energy, power, work, signal, and/or information produced by a system. (v) to provide, produce, manufacture, and/or generate.

pair—a quantity of two of something.
pass—to convey, transfer, and/or transmit.
perpendicular—intersecting at or forming substantially right angles.
place—to put in a particular place or position.
plane—a surface containing all the straight lines that connect any two points on it.
plurality—the state of being plural and/or more than one.
portion—a part, component, section, percentage, ratio, and/or quantity that is less than a larger whole. Can be visually, physically, and/or virtually distinguishable and/or non-distinguishable.
position—to put in place.
predetermined—established in advance.
prevent—to impede, hinder, stop, and/or keep from happening.
provide—to furnish, supply, give, convey, send, and/or make available.
ray—a narrow beam of light.
receive—to gather, take, acquire, obtain, accept, get, and/or have bestowed upon.
reflect—to throw back light from a surface.
regarding—pertaining to.
relative—considered with reference to and/or in comparison to something else.
responsive—reacting to an influence and/or impetus.
rim—a raised edge of an object.
said—when used in a system or device claim, an article indicating a subsequent claim term that has been previously introduced.
second—an entity immediately following a first entity in an ordering.
self-contained—a substantially complete and/or substantially independent unit.
sequentially—a in an ordered consecutive manner.
set—a related plurality of predetermined elements; and/or one or more distinct items and/or entities having a specific common property or properties.
shape—a characteristic surface, outline, and/or contour of an entity.
simultaneously—at substantially the same time.
slot—a narrow opening and/or aperture.
source—a device from which illumination originates.
standoff—a protrusion adapted to contact a surface upon which a device and/or system is operatively placed and position the device and/or system at a predetermined location relative to an object and/or point of reference.
status—a state and/or condition and/or information related thereto.
subsequent—following in time.
subset—a portion of a set.
substantially—to a considerable, large, and/or great, but not necessarily whole and/or entire, extent and/or degree.
support—to bear the weight of, especially from below.
surface—the outer boundary of an object or a material layer constituting or resembling such a boundary.
system—a collection of mechanisms, devices, data, and/or instructions, the collection designed to perform one or more specific functions.
through—in one side and out another side of.
toward—in a direction of.
transmit—to provide, furnish, supply, send as a signal, and/or to convey (e.g., force, energy, and/or information) from one place and/or thing to another.
truncate—to slice off a corner region of a polyhedron.
turn on—to put into operation and/or activate.
utilize—to use and/or put into service.
via—by way of and/or utilizing.
view—to observe and/or obtain an image.
wherein—in regard to which; and; and/or in addition to.
which—what particular one or ones.
without—not accompanied by.
with respect to—relative to.
zone—an area and/or region distinguished from adjacent parts by a distinctive feature and/or characteristic.

Note

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, description, abstract, drawing figure, etc.) of this application, unless clearly specified to the contrary, such as via explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

any elements can be integrated, segregated, and/or duplicated;

any activity can be repeated, any activity can be performed by multiple entities, and/or any activity can be performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

When any claim element is followed by a drawing element number, that drawing element number is exemplary and non-limiting on claim scope.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such material is specifically not incorporated by reference herein.

Accordingly, every portion (e.g., title, field, background, summary, description, abstract, drawing figure, etc.) of this application, other than the claims themselves, is to be regarded as illustrative in nature, and not as restrictive.

What is claimed is:

1. A self-contained imaging system comprising:
a dome, said dome having a truncated four-sided pyramid shape;
a crown adapted to be operatively coupled to an apex portion of said dome;
a plurality of light sources adapted to illuminate an object, each of said plurality of light sources located at a predetermined distance and a predetermined orientation relative to a viewing plane of a camera adapted to be supported by said dome and adapted to obtain an image of said illuminated object, said viewing plane perpendicular to a viewing axis of said camera, said plurality of light sources comprising:
   a set of low angle direct light sources operatively coupled to said dome, said low angle direct light sources adapted to illuminate said object via a set of apertures defined by said dome, said set of apertures adapted to cause light rays from said low angle direct light sources to intersect said viewing plane at an angle of approximately 30 degrees;
   a set of medium angle direct light sources attached to said dome, slots defined by said dome adapted to cause light rays from said medium angle direct light sources to intersect said viewing plane at an angle of approximately 45 degrees; and
   a light source that is directed toward said dome, said dome adapted to reflect light rays from said light source toward said viewing plane at an angle with respect to said viewing plane of between approximately 45 degrees and approximately 90 degrees, said light source comprising a rim that prevents light rays from said light source directed toward said dome from directly illuminating said object; and
   a light controller adapted to, responsive to information obtained via said camera, automatically illuminate at least one of said plurality of light sources to illuminate said object.

2. The system of claim 1, further comprising:
said object.

3. The system of claim 1, further comprising:
a circuit board adapted to transmit inputs and outputs between said camera and a device external to said camera.

4. The system of claim 1, further comprising:
a circuit board adapted to provide electrical energy to said camera.

5. The system of claim 1, further comprising:
a status indicator of at least one of said plurality of light sources.

6. The system of claim 1, further comprising:
a machine vision information device adapted to interpret said image.

7. The system of claim 1, further comprising:
said camera.

8. The system of claim 1, wherein:
said plurality of light sources comprises a diffuse on-axis light source from said plurality of light sources, said diffuse on-axis light source coupled to said crown and directed toward a beamsplitter, said beamsplitter adapted to reflect a portion of light rays from said diffuse on-axis light source at an angle that is approximately perpendicular to said viewing plane.

9. The system of claim 1, wherein:
one or more standoffs adapted to contact a surface upon which said system is operatively placed and position said system at a predetermined location relative to said object.

10. The system of claim 1, further comprising:
a lens associated with said camera.

11. The system of claim 1, wherein:
said plurality of light sources are light emitting diodes.

12. A method comprising:
via a light controller, responsive to information obtained via a camera, causing an automatic illumination of at least one of a plurality of light sources, each of said plurality of light sources adapted to illuminate an object in a field of view of said camera, each of said plurality of light sources located at a predetermined distance and a predetermined orientation relative to a viewing plane of said camera, said camera adapted to be supported by a dome and adapted to obtain an image of said illuminated object, said viewing plane perpendicular to a viewing axis of said camera, said plurality of light sources comprising:
   a set of low angle direct light sources operatively coupled to said dome, said dome having a truncated four-sided pyramid shape, said low angle direct light sources adapted to illuminate said object via a set of apertures defined by said dome, said set of apertures adapted to cause light rays from said low angle direct light sources to intersect said viewing plane at an angle of approximately 30 degrees;
   a set of medium angle direct light sources attached to said dome, slots defined by said dome adapted to direct light rays from said medium angle direct light sources, an angle defined by said light rays from said medium angle direct light sources and said plane approximately 45 degrees; and
   a light source that is directed toward said dome, said dome adapted to reflect light rays from said light source toward said viewing plane at an angle with respect to said viewing plane of between approximately 45 degrees and approximately 90 degrees, said light source comprising a rim that prevents light rays from said light source directed toward said dome from directly illuminating said object.

13. The method of claim 12, further comprising:
causing an illumination of said low angle direct light sources without illumination from additional light sources of said plurality of light sources.

14. The method of claim 12, further comprising:
obtaining said image of said object.

15. The method of claim 12, further comprising:
causing an illumination of said plurality of light sources sequentially.

16. The method of claim 12, further comprising:
causing an illumination of each of said plurality of light sources substantially simultaneously.

17. The method of claim 12, further comprising:
based upon an obtained image of said object, automatically determining which of said plurality of light sources to illuminate to obtain a subsequent image of said object.

18. The method of claim 12, wherein:
said plurality of light sources comprises a diffuse on-axis light source from said plurality of light sources operatively coupled to a crown, said crown operatively coupled to said dome, said diffuse on-axis light source directed toward a beamsplitter, said beamsplitter adapted to reflect a portion of light rays from said diffuse on-axis light source at an angle that is approximately perpendicular to said viewing plane.

19. A machine-readable medium comprising machine-implementable instructions for activities comprising:

via a light controller, responsive to information obtained via a camera, causing an automatic illumination of at least one of a plurality of light sources, each of said plurality of light sources adapted to illuminate an object in a field of view of said camera, each of said plurality of light sources located at a predetermined distance and a predetermined orientation relative to a viewing plane of said camera, said camera adapted to be supported by a dome and adapted to obtain an image of said illuminated object, said viewing plane perpendicular to a viewing axis of said camera, said plurality of light sources comprising:

a set of low angle direct light sources operatively coupled to a dome, said dome having a truncated four-sided pyramid shape, said low angle direct light sources adapted to illuminate said object via a set of apertures defined by said dome, said set of apertures adapted to cause light rays from said low angle direct light sources to intersect said viewing plane at an angle of approximately 30 degrees;

a set of medium angle direct light sources attached to said dome, slots defined by said dome adapted to direct light rays from said medium angle direct light sources, an angle defined by said light rays from said medium angle direct light sources and said plane approximately 45 degrees; and a light source that is directed toward said dome, said dome adapted to reflect light rays from said light source toward said viewing plane at an angle with respect to said viewing plane of between approximately 45 degrees and approximately 90 degrees, said light source comprising a rim that prevents light rays from said light source directed toward said dome from directly illuminating said object.

* * * * *